United States Patent [19]

Selenke

[11] Patent Number: 4,505,433

[45] Date of Patent: Mar. 19, 1985

[54] TISSUE GRINDING AND TRANSPORTING DEVICE

[76] Inventor: William M. Selenke, 18 Gambier Cir., Cincinnati, Ohio 45218

[21] Appl. No.: 425,509

[22] Filed: Sep. 28, 1982

[51] Int. Cl.³ ............................................. B02C 23/36
[52] U.S. Cl. ................................. 241/46 R; 128/749; 206/222; 241/169.1
[58] Field of Search ............... 241/2, 38, 46 B, 100, 241/169.1, 169.2, DIG. 27, 169, 283, 46 R; 128/749; 206/219, 222

[56] References Cited

U.S. PATENT DOCUMENTS

| | | | |
|---|---|---|---|
| 2,602,596 | 7/1952 | Jones et al. | 241/169.1 |
| 2,642,065 | 6/1953 | Negri | 206/222 X |
| 3,008,570 | 10/1961 | Roehr et al. | |
| 3,450,129 | 7/1969 | Avery et al. | |
| 3,835,835 | 9/1974 | Thompson et al. | |
| 3,941,317 | 3/1976 | Kanor | 241/2 X |
| 4,260,077 | 4/1981 | Schroeder | |

*Primary Examiner*—Mark Rosenbaum
*Assistant Examiner*—Joseph M. Gorski
*Attorney, Agent, or Firm*—Wood, Herron & Evans

[57] ABSTRACT

A device for grinding and transporting solids, such as surgical tissue samples, is disclosed which comprises in a preferred form a container having an upper portion defining an upwardly open top and a grinder receivable in the interior of the container. The grinder has a grinding head having a shape closely conforming to the shape of the container interior bottom, a cap that is screwed onto the upper portion of the container, and a compressible intermediate and body section joining the grinding head and the grinder top. A reservoir containing bacterial maintenance fluid, such as a frangible glass ampul containing such fluid, is carried within the compressible intermediate section.

The grinding device has a grinding configuration wherein the grinding head is received in the bottom interior of the container with the cap adjacent the container upper portion. In use, surgical tissue is placed in the container and the device is placed in the grinding configuration. Grinding is effected through application of the cap to the container upper portion to close the container, the cap forcing the grinding head into the bottom of the container interior and rotating it therein, thereby grinding tissue between the grinding head and the interior bottom. Compression of the intermediate portion of the grinder through the application of the cap to the container further places the glass ampul into compression and then breaks it, releasing the bacterial maintenance fluid to keep the tissue moist and reduce any molecular oxygen present.

19 Claims, 4 Drawing Figures

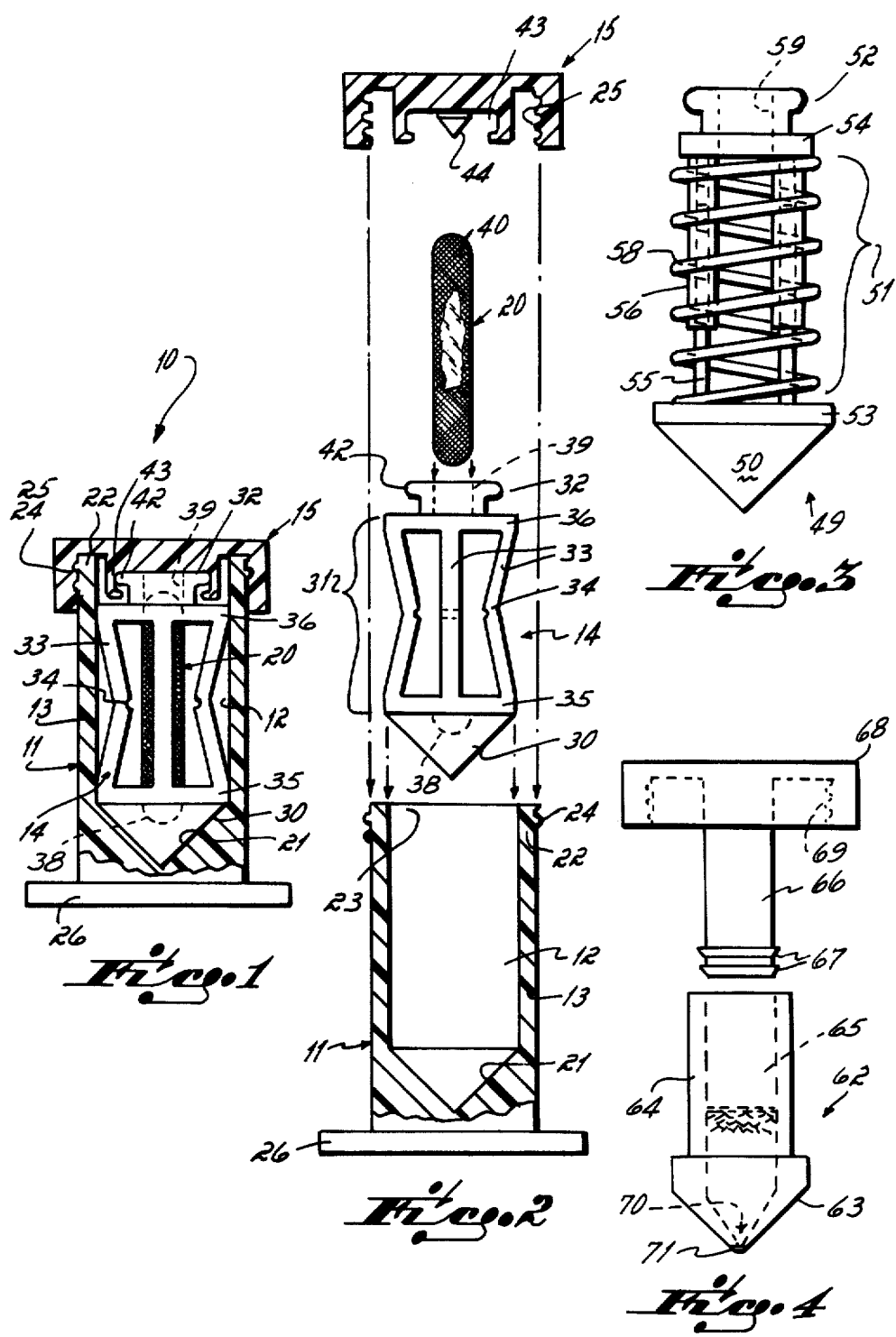

TISSUE GRINDING AND TRANSPORTING DEVICE

FIELD OF THE INVENTION

The present invention generally relates to a device for grinding solids, and more particularly to a device for the transportation and grinding of surgical tissue samples intended for microbiological examination, wherein the tissue sample is ground and transported within the same container.

BACKGROUND OF THE INVENTION

There are a variety of containers used to transport clinical specimens to a laboratory for testing and examination for various microorganisms or viruses. For instance, sputum is collected and transported in a variety of containers specifically designed to collect sputum. Body fluids, pus, etc., are commonly obtained with hypodermic needles and syringes, and are simply transported to the laboratory in the same syringe in which the specimen was collected. Some of the specimen transport containers serve a dual function in that the container itself is used in obtaining the specimen and/or has some contained means to initially operate on, preserve or otherwise maintain the specimen.

Of specific note is a popular swabbing system for collecting, preserving and transporting a culture sample, and commonly sold under the trademark CULTURETTE (Avery, et al., U.S. Pat. No. 3,450,129). This self-contained swabbing unit includes a cotton-tipped swab which is used to collect the culture sample, a flexible plastic tube within which the swab is stored before use and replaced for transport, and a frangible glass ampul filled with a culture preserving liquid. After a culture has been collected on the swab, the swab is replaced in the tube and the latter is squeezed adjacent the ampul to break the ampul and release the preserving liquid which moistens the swab and keeps the collected culture sample in live condition until laboratory tests have been performed.

In comparison to these dual-function containers which are generally designed to facilitate collection, handling, transport and preservation of the clinical specimens, tissues of various organs, bones, cartilidge, etc. obtained by surgical procedures are collected and transported to the laboratory in what can be best described as an ad hoc basis. That is, the tissue sample once obtained is typically placed in a handy container which is not altogether unsuited for collection and transport of the tissue sample, but is not specifically adapted to facilitate handling, transport and preservation of these types of tissue samples. For instance, the tissue sample simply may be placed in a CULTURETTE container to thereby maintain the tissue sample in a moist environment during transport, or the sample may be deposited in any closable container with some physiological fluid added thereto to keep the sample moist. It will be recognized that the tissue sample should ideally be kept in a moist, reducing environment to maintain microorganisms, especially anaerobic bacteria, in a viable state during the period of minutes to hours between the time the tissue is collected and the time it is processed in the laboratory. A satisfactory reducing liquid environment would be Modified Stuart's Bacterial Transport Medium containing a chemical such as thioglycolate, which serves to reduce the amount of molecular oxygen present in the liquid environment.

Difficulties and inconveniences arise when the tissue sample is transported to the laboratory for processing in an ad hoc container. First, the tissue must be ground or minced so that any microorganisms in the more central portions of the tissue will be released. To grind the sample, it must be first removed from the ad hoc transporting container and placed into a grinder, which can be either the classic mortar and pestle type or of the glass-walled type with a central, relatively close fitting internal plunger. The act of moving the tissue from the transporting container to the grinder is time consuming and inconvenient for the lab technician inasmuch as sterile forceps must be used; this is only exacerbated if the tissue must be retrieved from a long tube, such as a CULTURETTE container. In addition, the various parts of the tissue grinding apparatus must be sterile to prevent contamination of the tissue specimen.

There are also additional disadvantages in the current ad hoc system for handling, transporting, preserving and processing tissue samples. One is that of inadvertent contamination of the tissue specimen. It is a working rule of microbiology that each step in handling a specimen outside of a sterile environment can cause the contamination of the tissue. Thus, there is a small but real chance the tissue can be contaminated in transfer from the transport container to the grinding device, or by the grinding device itself.

Another disadvantage derives from the very time consuming and meticulous nature of the grinding procedure. In large, busy microbiological laboratories, the extra time required to grind tissues can be quite significant.

In view of these noted difficulties, it would be far more desirable if the tissue sample could be transported in a container specifically adapted to the handling, transport and preservation of such tissue samples; moreover, it would be ideal if the tissue sample could be ground in the transportation container itself, thereby permitting immediate testing of the specimen upon removal at the laboratory.

SUMMARY OF THE INVENTION

It is a primary object of the present invention to provide a device adapted for the transportation and grinding of a solid, such as a surgical tissue sample.

In light of the above difficulties and inconveniences presented by the ad hoc way that surgical tissue samples are currently handled, transported, preserved and processed, it is a further object to provide a device which is specifically adapted to receive a surgical tissue sample, to preserve the sample during transport, and to grind the sample without the sample being removed from the device.

Another object of the invention is to provide a closable container for the transportation of a solid, such as a surgical tissue sample, having a self-contained liquid reservoir therein for preserving the specimen in a moist environment, and an associated grinder which is receivable in the container to act upon and grind the sample.

Still a further object is to provide a simple and inexpensive device for use with a surgical tissue sample which serves to transport, preserve and grind the specimen all in a single container.

Yet another object is to provide a grinding device for surgical tissue specimens which simultaneously releases a contained liquid reservoir for maintaining a tissue specimen during transport in a moist environment and grinds the tissue specimen through the act of closing the container.

These and other objects are accomplished by the present invention in a device for transporting, preserving and grinding solids, such as surgical tissue samples or specimens, which includes an outer container having a generally cylindrically shaped open interior space defined within rigid side walls, and an upper portion having an upwardly open top. The container has an interior bottom which preferably is of a concave or conical shape, having a downwardly and inwardly sloping surface.

A grinder is receivable in the interior of the container, and comprises a grinding head having a rigid surface with a shape closely conforming to the shape of the container interior bottom, e.g., convex or conical, an intermediate and body portion, and a top portion including a cap receivable on the upper portion of the container to close the container. The device additionally has a fluid reservoir which is releasable within the container interior to provide a moist and preserving environment for a tissue sample deposited therein.

The device has a grinding configuration wherein the grinding head is received in the bottom interior of the container and the cap is adjacent the container upper portion. Grinding is effected through rotation of the cap with the downward application of force. Rotation of the cap in turn rotates the grinding head relative to the container interior bottom, grinding the tissue between the head and bottom.

In one form of the invention, the grinder intermediate and body portion is compressible, and further has a hollow therein for receiving a frangible glass ampul containing a tissue preserving liquid. The upper portion of the container has screw threads thereon, the cap being a screw-on cap receivable on the upper container portion. In the grinding configuration, the action of screwing on the cap to the upper portion compresses the body portion, the ampul being also compressed and thereby fracturing releasing the liquid contained therein into the container interior. The action of screwing on the cap further imparts rotary motion and downward force to the grinding head to effect grinding of the tissue sample.

Another form of the invention provides for a grinder which includes a barrel carrying the grinder head at one end. A cylindrical-shaped piston is receivable in the other end of the barrel and is in substantially fluid-tight engagement with the interior side walls of the barrel. A fluid reservoir is formed within the barrel and below the piston head, which communicates with a port extending through the grinding head, the port having a removable fluid-tight closure. The upper portion of the container is threaded, with the grinder cap being match-threaded for application and engagement of the cap to the container. In the grinding configuration of this form of the invention, the act of screwing on the cap to close the container advances the piston within the barrel, thereby forcing the fluid in the reservoir through the port and removable closure, while further serving to rotate the grinding head to effect grinding of the tissue sample.

It will thus be apparent that the present invention provides a simple and expedient means for handling, transporting, preserving and processing a tissue sample. The device promotes immediate testing of the specimen upon receipt at the laboratory without a need to remove the tissue sample from the transport container and then grinding the sample, which further eliminates any risk of contamination of the specimen through use of any grinding device ancillary to the transport container.

In addition, a self-contained liquid reservoir is included with the device which is releasable in the interior of the transport container to preserve the tissue specimen in a moist environment during transport. Time is thus saved since a source of preserving liquid is immediately available, and there is also no risk that the liquid will be omitted. In this latter regard, in a preferred form of the invention, the release of the liquid within the container interior as well as grinding of the tissue sample are simultaneously effected through the simple act of applying the cap to the upper portion of the container to close the container, thereby insuring that the liquid is released to bathe the tissue sample.

It will be understood that the cap which is receivable on the upper portion of the container may either be formed integral with the grinder or may alternatively be separable from the grinder. In the latter instance, the cap is receivable on the top portion of the grinder, such as through a snap connection, whereby the cap is adjacent the top of the grinder in the grinding configuration and fixedly engages the top of the grinder during application of the cap to the upper portion of the container in a manner to thereby transmit rotary motion to the grinding head. The cap may be supplied pre-assembled with the grinder, of course.

It will also be understood that the closure for the container need not be a screw-type engagement of the cap to the upper portion of the container, but also includes, for example, a two-stage snap-type closure whereby the closing of the container and compression of the grinder and release of the fluid reservoir are accomplished in a first closing step, with the cap thereafter free to rotate to thereby effect rotation of the grinding head for grinding.

The foregoing objectives, features and advantages of the present invention will be more readily understood upon consideration of the following detailed description of the invention taken in conjunction with the accompanying drawings, in which:

BRIEF DESCRIPTION OF THE DRAWINGS

FIG. 1 is an elevational view partly in section of a first embodiment of a tissue grinding and transporting device made in accordance with the principles of this invention.

FIG. 2 is a disassembled elevational view partly in section of the first embodiment of the grinding and transporting device.

FIG. 3 is an elevational view of a second embodiment of a grinder made in accordance with the principles of this invention.

FIG. 4 is an elevational view of a third embodiment of a grinder made in accordance with the principles of this invention.

DETAILED DESCRIPTION OF THE INVENTION

As shown in the drawings and for purposes of illustration, the grinding and transporting device of this invention is generally indicated at 10 of FIG. 1. The device is primarily adapted for the handling, transportation, preservation and processing of a solid, and particularly a surgical tissue sample or specimen, and provides for the grinding of the solid within the transporting container itself. The principal elements of the device 10 comprises an outer container 11 having an interior space 12 defined between rigid side walls 13 and a grinder generally indicated at 14 having cap 15 which is receivable on the upper portion of the container 11 and which engages the top 32 of the grinder. The fluid reservoir shown in this first embodiment of the grinder 14 is constituted by a frangible vial or ampul 20 which is carried within the grinder 14 in a manner to be more specifically described below.

Common to all of the embodiments of the grinder which will be hereinafter described in detail is the outer container 11. The container 11 is preferably of a cylindrical shape and formed of a rigid plastic. For ease of manufacture and in keeping the expense of the device low, plastic is advantageously employed for all of the components of the device.

The interior space 12 defined within the rigid side walls 13 is also preferably cylindrical in form. As best shown in FIG. 2, the interior bottom 21 of the container 11 is preferably of a concave, or as here, conical, shape to facilitate grinding of a tissue specimen which is deposited within the container interior 12 and which will ordinarily settle in the interior bottom 21. Of course, the configuration of the bottom is not limited to this conical shape, but may be convex, flat, etc. The interior bottom 21 may be smooth, as here, or may be provided with appropriate serrations (not shown) to facilitate grinding of a specimen.

The container 11 has an upper portion 22 which defines an upwardly open mouth 23 to the container 11 and interior space 12. Screw threads 24 are preferably formed around the exterior of the upper portion 22, and cooperate with matched screw threads 25 on the interior of the cap 15 to securely fasten the cap 15 to the upper portion 22 of the container to thereby close the container. A base 26 may additionally be provided for the container 11 to promote better stability of the container, particularly in the grinding configuration to be hereinafter described.

A first embodiment of the grinder, generally indicated at 14, has a grinding head 30, an intermediate and elongate body portion 31, and a top 32. The grinder 14 is preferably formed as a single unit, but this is a matter of manufacturing preference.

The grinding head 30 is a rigid element which is formed to be received in the interior bottom 21 of the container 11. The grinding head is shaped to substantially conform to the shape of the interior bottom 21, having a conical exterior surface shape similar to that of the interior bottom 21 and adapted to be received therein in generally surface-to-surface relation. The exterior surface of the grinding head 30 can be smooth as here, or may be provided with serrations or the like (not shown) to facilitate grinding of a sample deposited within the container bottom 21.

In this embodiment of the grinder 14, the body portion 31 is formed of a plurality of semi-rigid elongate portions 33. As illustrated herein, the elongate portions 33 are four in number, being regularly spaced from and generally extending along the longitudinal axis of the grinder 14. The members 33 extend between a lower portion 35 and an upper portion 36 of the intermediate body portion 31. The members 33 are provided with an inwardly facing notch 34 at a point approximately equidistant between the lower portion 35 and the upper portion 36. This notch 34 promotes the compression of the intermediate body portion 31 when a force is applied to the top 32 and/or top portion 36 by permitting the members 33 to bend inwardly and toward the longitudinal axis of the grinder 14. The members 33 are, however, rigid enough to transmit an axial rotation force applied to the top 32 of the grinder to the grinding head 30.

In accordance with one aspect of the present invention, the grinder 14 carries its own sealed reservoir of liquid for moistening the tissue sample which has been deposited in the container 11. Providing the grinder with its own self-contained reservoir does away with the need for pouring a separate moisturizing agent into the container to keep the microbiological organisms in the tissue sample in a live state, and also insures that the moisturizing agent is available when the device is employed. A preferred moisturizing liquid would be Modified Stuart's Bacterial Transport Medium containing a chemical such as sodium-thioglycolate to provide a suitable reducing environment to facilitate preservation of anaerobic bacteria contained in the tissue sample.

The grinder 14 is adapted to receive therein an elongate frangible glass ampul or vial 20. The ampul is received in a hollow defined by an appropriately shaped cavity 38 formed in the interior of the grinding head 30 and a tubular-shaped conduit 39 formed in the top 32. Formation of the ampul receiving hollow (38, 39) in this fashion facilitates the insertion of the vial 20 into the central part of the grinder 14. The ampul 20 is preferably made of a thin glass and is elongate, having a suitable covering such as cloth mesh 40 to contain any glass fragments which result upon the breaking or crushing of the vial 20.

The ampul 20 is securely carried in the hollow 38, 39 of the grinder 14, and can be advantageously placed therein through insertion through the tubular conduit 39. It will be noted that one end of the ampul 20 when secured in the grinder, preferably extends within a substantial portion of the conduit 39 for a reason to be hereinafter made clear.

The top 32 of the grinder is made integral with the upper portion 36 of the intermediate and body portion 31. The top 32 is generally cylindrical in shape, with the tubular conduit 39 defined therein between interior side walls. The top 32 has an outwardly and radially extending flange or lip 42 which surrounds the top. This lip 42 is received in a snap-type fitter 43 formed on the inside of the separable cap 15. The fitter 43 is a snap-type attachment, which engages the lip 42 of the top 32 in a tight frictional embrace when applied thereto. The cap 15 and fitter 43 may be formed of any suitable material, such as semi-rigid plastic.

In use, the device of this invention is initially placed in what can be described as a grinding configuration. That is, with a tissue sample deposited in the bottom interior 21 of the container 11, the grinder 14 with the ampul 20 mounted therein is placed within the interior space 12 of the container 11 with the grinding head 30 received in the interior bottom 21 as spaced therefrom by a tissue specimen (not shown). The cap 15 is then placed adjacent the upper portion 22 of the container 11, and the grinder top 32, so that the cap can be applied thereon.

With the device thus placed in the grinding configuration, release of the liquid within the ampul 20 and grinding of the tissue specimen are accomplished in this preferred embodiment through the simple act of screwing the cap 15 onto the upper portion 22, thereby closing the container 11 for transport. More specifically, as the cap is initially screwed onto the upper portion of the container 22, the snap fitter moves downwardly and toward the interior bottom 21. The grinder 14 is so sized relative to the container 11 and fitter 43 that a snap attachment and engagement between the fitter 43 and the top 32 of the grinder occurs at an early point in the application of the cap 15 to the container. Alternatively, the cap 15 may be supplied for use already engaged with the top of the grinder 32 through the previous application of the fitter 43.

As the cap 15 is further screwed onto the upper portion 22 through interaction of the threads 24 and 25, additional downward force exerted against the grinder 14 causes the members 33 of the intermediate and body portion 31 to be compressed and move inwardly. Furthermore, as the cap 15 is turned in its application to the upper portion 22 of the container 11, rotary motion is transferred to the grinding head 30 by virtue of the tight snap fit between the snap fitter 43 of the cap 15 and the top 32 of the grinder 14. The downward force applied by the application of the cap to the container further provides a downward force to the grinding head 30.

The combination of the downward and rotary forces applied to the grinding head 30 serves to grind and/or mince the tissue specimen between the grinding head 30 and the interior bottom 21 of the container.

Almost simultaneously with the initial application of the cap 15 to the upper portion 22 of the container 11 and the commencement of compression of the intermediate and body portion 21 of the grinder 14, the elongate ampul 20 will also be put under compression. This is a result of the snap-fitter 43 and the grinder to 32 moving downwardly as the cap is screwed onto the container, the ampul thereupon becoming wedged between the snap fitter 43 and the interior of the grinding head 30. A compression member or nub 44 may be advantageously formed downwardly depending from the snap fitter 43 to engage the ampul 20 at an earlier point to thereby hasten the compression of the ampul. At a certain point, and before the cap 15 is fully engaged with the container 11, the compressive forces upon the ampul 20 causes it to break or shatter, thereby releasing the liquid contained therein which is free to flow through the generally open intermediate and body portion 33 and into the container interior 12 to thereby moisten and preserve the tissue specimen. The cloth covering 40 contains the glass fragments of the now broken ampul.

FIG. 1 shows the device in a condition where the cap 15 has been fully applied to the upper portion 22 of the container and has thereby closed the container, with the grinder intermediate and body portion 31 compressed and the ampul 20 shattered. The entire device can now be transported to the laboratory for the testing of the tissue specimen which is maintained by the liquid released from the ampul 20. Once at the laboratory, the cap 15 is simply unscrewed and the cap 15 and attached grinder 14 removed, leaving the tissue specimen in the readily accessible bottom portion 21 of the container 11.

From the foregoing, it will be apparent that the grinding and transport device of this invention is far more convenient to use than the ad hoc arrangements previously employed in the handling, transport, preserving and processing of surgical tissue samples. The device is relatively simple in construction and formed of low-cost components which lend themselves to easy manufacture and assembly. A single container is used to both transport and grind the tissue sample, thereby eliminating any risk of contamination of the specimen through the use of multiple containers in the movement of the sample between containers. Since the container has its own liquid reservoir, there is no need to have on hand an additional moisturizing agent. The grinding and transport device of this invention also simply and expeditiously accomplishes the grinding of the tissue and the application of the moisturizing agent to the tissue through the simple act of applying a cap to the container and screwing it closed, making these operations automatic with the act of closing the container.

The grinder employed in this device may take a variety of forms. For example, a second embodiment of the grinder illustrated in FIG. 3 comprises a grinding head 50, intermediate and body portion 51, and a top portion 52. The grinding head 50 and top portion 52 are similar in structure to the grinding head 30 and top portion 32 described in relation to the first embodiment of the grinder 14, and will therefore not be described in further detail with regard to this embodiment.

The intermediate and body portion 51 of the second embodiment includes a lower and disc-shaped portion 53 which is made integral with the grinding head 50, and an upper and disc-shaped portion 54 which is made integral with the top 52. A pair of elongate rods 55 extend upwardly from the lower portion 53 and are fixed in parallel spaced relation to each other. The upper portion 54 has a complimentary pair of downwardly depending sleeves or tubes 56 in which the rods 55 are received for sliding movement therein. The top 52, upper portion 54 and sleeves 56, combined serve as a unitary sliding member on the rods 55.

A biasing member, such as the coil spring 58, extends between the upper and lower portions 54 and 53, respectively. One end of the spring abuts the lower portion 53 and the other end of the spring abuts the upper portion 54, thereby biasing the top 52 against movement toward the lower end of the grinder 49. A downwardly directed force against the top 52 will, however, compress the spring and therefore, the intermediate portion 51. This compressibility is, of course, necessary in this form of the invention to break a vial or ampul of liquid, like the ampul 20, which is carried in the central portion of the grinder 49 in a manner similar to that previously disclosed in relation to the grinder 14. A tubular conduit 59 is formed in the top 52 and upper portion 54 to facilitate insertion of and to carry the frangible ampul in the central area of the grinder 49.

It will be understood that the rods 55 and the sleeves 56 can be alternatively fixed to the upper portion 54 and lower portion 53, respectively, with equally advantageous results. Grinding, and the release of the liquid contained within the ampul carried by the second embodiment of the grinder 49, is effected in an equivalent manner to that described in relation to the first embodiment, and reference should therefore be made to that foregoing description.

A third embodiment of a grinder which can be advantageously used in the practice of this invention is generally indicated at 62 of FIG. 4. This grinder 62 differs from the two previously described embodiments partly in that the liquid reservoir is not contained within a frangible ampul, but is rather held within a reservoir formed within the grinder 62.

In this form of the invention, the grinder 62 comprises a grinding head 63 which is carried at one end of an intermediate and barrel portion 64 which defines within interior side walls a chamber 65. A piston 66 is receivable within the interior chamber 65 of the barrel 64 through insertion in the other end of the barrel. The piston 66 has one or more outwardly projecting concentric flanges 67 which serve to engage the interior side walls of the barrel 64 in a fluid-tight frictional fit. Fixed at the opposite end of the pistion 66 is a cap 68 having interior threads 69 which are matched to the threads 24 of the container upper portion 22.

The chamber 64 communicates with a port 70, shown here formed at the apex of the conical-shaped grinding head 63. The port 70 is closed by a removable fluid-tight closure 71, such as a small piece of thin plastic or the like adhered over the exterior of the port. With the port 70 thus closed by the removable closure 71, a reservoir of liquid can be maintained within the chamber 65 which is releasable to maintain the tissue sample in a moist environment.

The grinding configuration for this embodiment of the invention including the grinder 62 constitutes placing the tissue specimen within the interior bottom 21 of the container 11 with the grinder 62 thereafter inserted in the interior space 12 with the grinding head 63 received in the interior bottom 21, as slightly separated therefrom by the tissue specimen therein. The grinder 62 would be preferably provided to the user with the piston 66 partially inserted into the chamber 65. The cap 68 is adjacent the upper portion 22 of the container 11.

In a manner similar to that described in relation to the first embodiment, grinding and release of the liquid reservoir is accomplished through application of the cap 68 to the upper portion of the container 22. Downward motion of the cap 68 forces the piston 66 downwardly in the chamber 65, thereby forcing the liquid to break the seal of the removal closure 71 and flow out through the port 70 into the interior 12 of the container 11. Rotation of the piston 66 through the screw application of the cap 68 to the upper portion 22 of the container 11 is transmitted to the barrel 64 of the grinder 62 through the friction fit maintained by the flanges 67, thereby rotating the grinder head 63. The interior side walls of the barrel 64 may be roughened to promote this frictional fit. The downward and rotational forces transmitted to the grinder head 63 through application of the cap 68 in closing the container 11 serves to grind the tissue wedged between the surface of the grinding head 63 and the interior bottom surface 21 of the container 11.

As illustrated in the third embodiment of the grinder depicted in FIG. 4, the cap of the grinder need not constitute a separable component of the device. The cap may either be a separable cap such as cap 15, which snap-fits to the top 32 or 52 of a grinder, or integrally formed with the grinder proper, such as cap 68.

Likewise, it will be understood that a cap need not be applied to the container through a screw-on fit, the invention encompassing any kind of closure arrangement whereby a cap or cap-like closure will apply downward or compression force to drive the grinding head into the interior bottom of the container while also transmitting a rotational force to the grinding head to thereby effect grinding of a tissue sample.

As described herein, the foregoing embodiments of the invention accomplish release of the liquid reservoir and grinding simultaneously with the closing of the container. These two procedures need not be simultaneous to come within the scope of this invention, however, but may consist of a two or more step process. For example, a snap-on type cap may be employed whereby a first step constitutes an initial application of the cap to the container to thereby release the liquid reservoir and force the grinding head into the bottom interior of the container, with a second step comprising the free and unlimited rotation of the grinding head through rotation of the snap-on cap.

Thus, while the invention has been described in connection with certain presently preferred embodiments, it will be immediately obvious to those skilled in the art many modifications of structure, arrangement, portions, elements, materials, and components used in the practice of the invention which are particularly adapted for specific environments without departing from the principles of this invention.

What is claimed is:

1. A device for grinding solids, such as surgical tissue samples, comprising:
   a container, the container having an interior defined within sidewalls, an upper portion having an upwardly open top, and an interior bottom;
   a grinder receivable in the interior of the container, the grinder comprising,
   a grinding head
   a body portion having an interior space defined therein,
   a cap receivable in the upper portion of the container; and
   a closed fluid reservoir located within the interior space of the body portion;
   at least one port in the grinder through which fluid can pass into the container;
   the grinder and container having a grinding configuration wherein the grinding head is located adjacent the bottom interior of the container and the cap is applied to the container upper portion placing the grinder under compression, release of fluid from the closed reservoir being effected through application of the cap to the container upper portion to thereby rupture the fluid reservoir releasing the fluid, grinding being effected through rotation of the cap, the cap further serving to close the container.

2. The grinding device of claim 1 wherein the grinder further includes a barrel, a piston having a piston head receivable in the barrel, means for providing a substantially fluid-tight fit between and a barrel and piston, and a fluid reservoir formed within the barrel and below the piston head, the reservoir communicating with a port extending through the grinding head, the port having a removable fluid-tight closure.

3. The grinding device of claim 2 wherein the fluid is released from the fluid reservoir by advancing the piston head within the barrel to thereby forcibly move the liquid through the port and closure and into the container.

4. The grinding device of claim 2 wherein the means for providing a substantially fluid-tight fit between the barrel and piston constitutes at least one semi-rigid annular flange concentric with the piston, the flange being in frictional and substantially fluid-tight engagement with the interior walls of the barrel in the grinding configuration.

5. The grinding device of claim 2 wherein the cap and the container upper portion are match-threaded for screw application of the cap to the container, and wherein the act of screwing on the cap advances the piston within the barrel, thereby forcing the fluid in the reservoir through the port and closure, while further rotating the grinding head to effect grinding and also closing the container.

6. The grinding device of claim 1 wherein the body portion has an upper and a lower end, and includes plural spaced semi-rigid elements extending between the upper and lower ends thereof, the semi-rigid elements bending radially relative to the body portion when the body portion is under compression.

7. The grinding device of claim 6 wherein the cap is separable from the grinder, the fluid reservoir is a rupturable ampul, the lower end of the body segment carrying the grinding head, the upper end having means thereon to fixably receive and engage the cap, the body portion having an opening in its upper end through which the interior space can be accessed and through which opening the rupturable ampul can be inserted into the interior space.

8. A device for grinding solids, such as surgical tissue samples, comprising:
 a container, the container having an interior defined within sidewalls, an upper portion having an upwardly open top, and an interior bottom;
 a grinder receivable in the interior of the container, the grinder comprising,
  a grinding head,
  a cap receivable on the upper portion of the container,
  an elongated body portion having an upper and a lower end, the lower end of the body portion carrying the grinding head, the upper end having means thereon to fixedly receive and engage the cap;
  a frangible glass ampul having fluid therein, the ampul having means thereon to retain broken glass, the ampul being mountable in the body portion of the grinder;
 the upper portion of the container and the cap having matching screw threads for application of the cap to the container;
 the grinder and container having a grinding configuration wherein the grinding head is received in the bottom interior of the container and the cap is applied to the container upper portion placing the grinder under compression, application of the cap to the container breaking the ampul in the grinding configuration, grinding being effected by screwing the cap onto the container, the cap further serving to close the container.

9. The grinding device of claim 8 wherein the elongated body portion is compressible along its longitudinal axis, the body portion being compressed in the grinding configuration when acted upon through screwing of the cap to the container, the ampul being compressed and thereby fractured when acted upon through screwing of the cap to the container.

10. The grinding device of claim 9 wherein the elongated body portion includes plural spaced semi-rigid elements extending between the upper and lower ends thereof, the semi-rigid elements bending radially relative to the body portion when the body portion is under compression.

11. The grinding device of claim 10 wherein the container interior bottom is generally concave in shape, the grinding head being generally convex in shape and receivable in the container bottom in approximate surface-to-surface contact.

12. A device for grinding solids, such as surgical tissue samples, comprising:
 a container, the container having an interior defined with sidewalls, an upper portion having an upwardly open top, and an interior bottom;
 a grinder receivable in the interior of the container, the grinder comprising:
  a grinding head,
  a cap receivable on the upper portion of the container,
  an elongated body portion carrying the grinding head on a lower end, the upper end having means thereon to fixedly engage the cap, the cap being separable from the grinder;
  a frangible glass ampul having fluid contained therein, the ampul being mountable within the body portion of the grinder, the body portion further being compressible along its longitudinal axis;
 the grinder and container having a grinding configuration wherein the grinding head is received in the bottom interior of the container and the cap is applied to the container upper portion placing the grinder under compression, grinding being effected through rotation of the cap, the cap further serving to close the container.

13. The grinding device of claim 12 wherein application of the cap to the container places the ampul into compression to thereby fracture the ampul, the ampul further including means thereon to substantially contain any glass fragments resulting from such fracturing.

14. The grinding device of claim 13 wherein the grinder body portion comprises two elongate rods extending in parallel spaced relation partway between the upper and lower ends of the body segment, the rods being fixedly mounted at one end to one of the upper and lower ends, a slidable member mounted for limited longitudinal movement relative to the rods, and a spring extending between the upper and lower ends of the body segment.

15. The grinding device of claim 14 wherein the slidable member comprises a disk having downwardly depending sleeves receivable on the elongate rods, the spring abutting the bottom of the disk and the lower end of the body portion, the spring surrounding the rods and sleeves.

16. A device for grinding and transporting solids, such as surgical tissue samples, comprising:
 an outer container, the outer container having interior sidewalls defining an interior bottom portion space, an upwardly open top to the sidewalls, an interior presenting a grinding surface, and screw threads adjacent the open top,
 a grinder receivable in the interior space of the outer container, the grinder comprising a grinding member having a surface complementing the surface of the container interior bottom, a top, and a compressible intermediate portion joining the grinding member and top of the grinder,
 a reservoir of liquid carried within the intermediate portion,
 a screw-on cap receivable on the outer container top, the cap having matched threads to the threads of the outer container top, the cap being interconnected with the grinder top;
 so that a solid placed within the interior space can be ground and a liquid applied to the tissue by inserting the grinding member into the interior space of the outer container and screwing on the screw-on cap.

17. A grinding device comprising:
a container having an interior bottom portion and an upper portion defining an opening,
a grinder having a grinding head, a body portion and a cap operable as a closure for the container opening, the grinding head being received in the interior bottom portion of the container when the grinder is substantially in the container and when the cap is adjacent the upper portion of the container, thereby defining a grinding configuration in which rotation of the cap rotates the grinding head to thereby effect grinding,
a frangible reservoir containing a fluid,
the grinder body portion having an interior space defined therein within which the reservoir is located, and
means for releasing the fluid from the frangible fluid reservoir and into the container when the cap is applied to the container to close the container device is placed in the grinding configuration.

18. A device for grinding solids, such as surgical tissue samples, comprising:
a container having an interior defined within sidewalls, an upper portion having an upwardly open top, and an interior bottom;
a grinder receivable in the interior of the container, the grinder comprising,
a grinding head,
a body portion,
a cap receivable in the upper portion of the container,
a frangible reservoir containing liquid;
the body portion of the grinder having a space defined therein wherein the reservoir is located, the grinder having at least one port through which the liquid can pass into the container when the frangible reservoir is broken;
the grinder and container having a grinding configuration wherein the grinding head is located adjacent the bottom interior of the container and the cap is adjacent the container upper portion, release of the liquid into the container from the frangible reservoir being effected by application of the cap to the container to close the container, and grinding being effected through rotation of the cap on the container.

19. The grinding device of claim 18 wherein the body portion is elongated and is compressible along its longitudinal axis, the body portion being compressed in the grinding configuration through application of the cap to the container, the frangible reservoir being thereby also compressed and broken to release liquid into the container.

* * * * *

UNITED STATES PATENT AND TRADEMARK OFFICE
CERTIFICATE OF CORRECTION

PATENT NO. : 4,505,433  Page 1 of 3
DATED : March 19, 1985
INVENTOR(S) : William M. Selenke It is certified that error appears in the above-identified patent and that said Letters Patent is hereby corrected as shown below:

The ABSTRACT of the disclosure should read as follows:

A device for grinding and transporting solids, such as surgical tissue samples includes a container having an upper portion defining an upwardly open top and a grinder receivable in the interior of the container. The grinder has a grinding head, a cap that is screwed onto the upper portion of the container, and a compressible body portion joining the grinding head and the grinder top. A fluid reservoir, such as a frangible glass ampul containing bacterial maintenance fluid, is carried within the compressible intermediate section. A grinding configuration is defined wherein the grinding head is received in the bottom interior of the container with the cap adjacent the container upper portion. In use, surgical tissue is placed in the container and the device is placed in the grinding configuration. The cap is applied to the container upper portion to close the container. This forces the grinding

UNITED STATES PATENT AND TRADEMARK OFFICE
CERTIFICATE OF CORRECTION

PATENT NO. : 4,505,433

DATED : March 19, 1985

INVENTOR(S) : William M. Selenke

It is certified that error appears in the above-identified patent and that said Letters Patent is hereby corrected as shown below:

head into the bottom of the container interior and rotates it therein, thereby grinding tissue between the grinding head and the interior bottom. The body portion of the grinder is also compressed, which places the glass ampul into compression and then breaks it, releasing the bacterial maintenance fluid to keep the tissue moist and reduce any molecular oxygen present.

Column 5, line 1 "comprises" should be --comprise--.

Column 7, line 31 "to 32" should be --top 32--.

Column 10, line 44 delete the first occurrence of "and a" should be --the--.

Column 10, line 44 delete the second occurrence of "and" should be --the--.

Column 10, line 45 delete "a".

Column 12, line 48 delete "bottom portion".

Column 12, line 50 After "interior" insert --bottom portion--.

UNITED STATES PATENT AND TRADEMARK OFFICE
CERTIFICATE OF CORRECTION

PATENT NO. : 4,505,433
DATED : March 19, 1985
INVENTOR(S) : William M. Selenke

It is certified that error appears in the above-identified patent and that said Letters Patent is hereby corrected as shown below:

Column 13, line 19  insert --the-- before "device".

Signed and Sealed this

Twenty-second Day of October 1985

[SEAL]

Attest:

DONALD J. QUIGG

Attesting Officer

Commissioner of Patents and
Trademarks—Designate